US012734254B2

(12) United States Patent
Garavaglia et al.

(10) Patent No.: US 12,734,254 B2
(45) Date of Patent: Sep. 15, 2026

(54) PROBE DIRECTED TO ENZYME ALDH1A3 AND USE THEREOF IN THE DIAGNOSIS OF GLIOBLASTOMA

(71) Applicants: Universita' Degli Studi Del Piemonte Orientale "A. Avogadro", Vercelli (IT); Universita' Degli Studi Di Pavia, Pavia (IT)

(72) Inventors: Silvia Garavaglia, Vercelli (IT); Menico Rizzi, Vercelli (IT); Alberto Minassi, Vercelli (IT); Diego Caprioglio, Vercelli (IT); Edoardo Luigi Maria Gelardi, Vercelli (IT); Giorgia Colombo, Vercelli (IT); Lorenzo Magrassi, Pavia (IT)

(73) Assignees: Universita' Degli Studi Del Piemonte Orientale "A. Avogadro", Vercelli (IT); Universta' Degli Studi Di Pavia, Pavia (IT)

( * ) Notice: Subject to any disclaimer, the term of this patent is extended or adjusted under 35 U.S.C. 154(b) by 510 days.

(21) Appl. No.: 18/285,713

(22) PCT Filed: Apr. 6, 2022

(86) PCT No.: PCT/IB2022/053216

§ 371 (c)(1),
(2) Date: Oct. 5, 2023

(87) PCT Pub. No.: WO2022/214995

PCT Pub. Date: Oct. 13, 2022

(65) Prior Publication Data

US 2025/0281649 A1 Sep. 11, 2025

(30) Foreign Application Priority Data

Apr. 6, 2021 (IT) ........................ 102021000008504

(51) Int. Cl.
*A61K 49/00* (2006.01)
*A61P 35/00* (2006.01)
(Continued)

(52) U.S. Cl.
CPC .......... *A61K 49/0021* (2013.01); *A61P 35/00* (2018.01); *C07D 249/04* (2013.01); *C07F 9/09* (2013.01)

(58) Field of Classification Search
CPC ............ A61K 49/0019; A61K 49/0021; A61K 49/003
See application file for complete search history.

(56) References Cited

U.S. PATENT DOCUMENTS

2013/0261121 A1 10/2013 Shih
2018/0362433 A1 12/2018 Laali (Continued)

FOREIGN PATENT DOCUMENTS

WO 2014145493 A1 9/2014
WO 2017218219 A1 12/2017

OTHER PUBLICATIONS

PCT International Search Report and Written Opinion for PCT Patent Application No. PCT/IB2022/053216 mailed Jun. 3, 2022.

(Continued)

*Primary Examiner* — Micah Paul Young
(74) *Attorney, Agent, or Firm* — Lathrop GPM LLP; Malaika O.D. Tyson

(57) ABSTRACT

The present invention relates to compounds of formula (I), wherein X is —OH, —$N(CH_3)_2$, (II) or (III) or (IV): Y is CH or N; and Z is (V), (VI), (VII), (VIII) or (IX) and salts, solvates and solvates of the salts thereof.

(I)

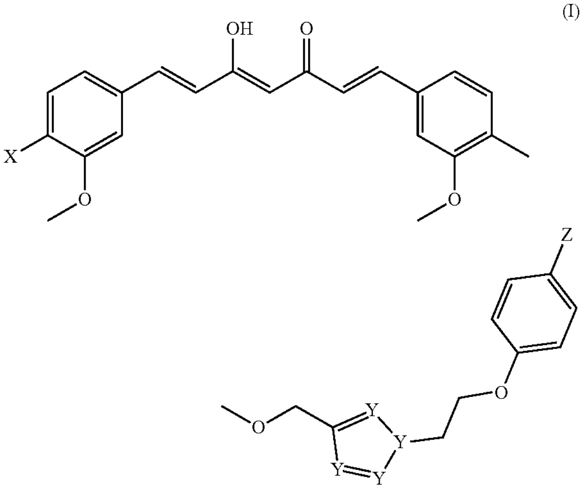

(II)

(III)

(IV)

(V)

(Continued)

-continued (VI)

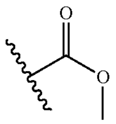

(VII)

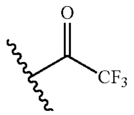

(VIII)

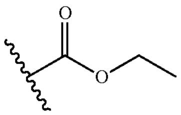

(IX)

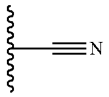

8 Claims, 2 Drawing Sheets

(51) Int. Cl.
*C07D 249/04* (2006.01)
*C07F 9/09* (2006.01)

(56) References Cited

U.S. PATENT DOCUMENTS

2020/0199092 A1 6/2020 Bearrood
2020/0207989 A1 7/2020 Urano

OTHER PUBLICATIONS

Klaus Pors et al: "Aldehyde dehydrogenases in cancer: an opportunity for biomarker and drug development?", Drug Discovery Today, vol. 19, No. 12, Dec. 1, 2014 (Dec. 1, 2014), pp. 1953-1963, XP055381076, Amsterdam, NL.

Jordan Brian C. et al: Synthesis, evaluation of cytotoxic properties of promising curcumin analogues and investigation of possible molecular mechanisms, Chemical Biology & Drug Design.

Lin L et al: "Antitumor Agents. 250. Design and Synthesis of New Curcumin Analogues as Potential Anti-Prostate Cancer Agents", Journal of Medicinal Chemistry, vol. 49, No. 13, Jul. 1, 2006 (Jul. 1, 2006). pp. 3963-3972, XP008110105, DOI: 10.1021/JM051043z.

PROBE DIRECTED TO ENZYME ALDH1A3 AND USE THEREOF IN THE DIAGNOSIS OF GLIOBLASTOMA

CROSS-REFERENCE TO RELATED APPLICATIONS

The present application is filed pursuant to 35 U.S.C. 371 as a U.S. National Phase application of International Patent Application No. PCT/IB2022/053216, which was filed Apr. 6, 2022, claiming priority to Italian Patent Application No. 102021000008504 filed on Apr. 6, 2021, the entire disclosure of each is incorporated herein by reference.

TECHNICAL FIELD OF THE INVENTION

The present invention relates to a compound of formula (HGG) are distinguished by their aggressiveness and resistance to chemo- and radiotherapy treatments and are characterized by a poor prognosis. The malignancy increase is related to the presence of cancer stem cells (CSCs) which are the proliferating constituent element of the neoplasm and from which other cancer cells differentiate. Clinical management of glioblastoma, including diagnosis, assessment of growth, postoperative outcome and efficacy of therapy, are based mostly on neurological assessment and clinical imaging techniques, such as magnetic resonance imaging, CT, PET and biopsy tissue sampling.

Recent studies highlighted the increase of expression and enzyme activity in CSCs of the protein aldehyde dehydrogenase1A3 (ALDH1A3) and its correlation with a negative prognostic outcome for many solid tumours, including HGG. Importantly, several experimental evidences indicate that ALDH1A3 is a key protein involved in

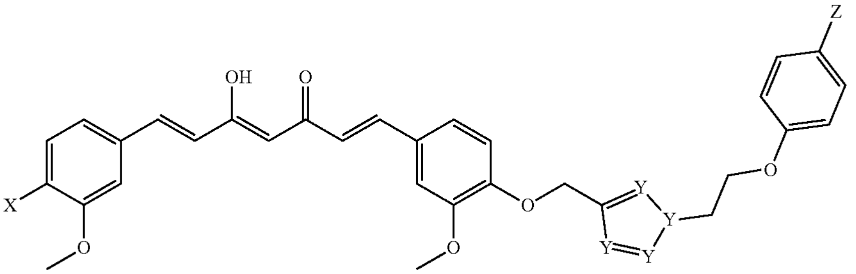

wherein

X is —OH, $—N(CH_3)_2$,

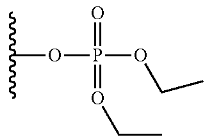

or

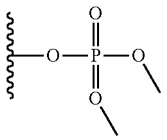

or

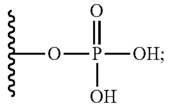

Y is CH or N; and

Z is

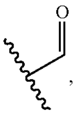

,

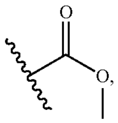

,

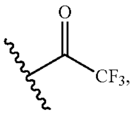

,

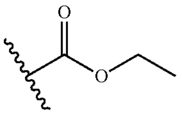

or

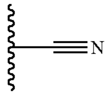

and salts, solvates and solvates of the salts thereof, which is used as a fluorescent probe selective for enzyme ALDH1A3.

STATE OF THE ART

Gliomas make up about 70% of malignant brain tumours. Among them, gliomas with a high degree of malignancy cell proliferation, survival and chemo/radio resistance of CSCs. It is a NAD-dependent enzyme capable of oxidizing retinaldehyde to the respective carboxylic acid and is part of a superfamily of proteins composed of 19 isoenzymes (ALDHs) with a different cytosolic and tissue distribution, and able to act on specific substrates. The 19 families of ALDHs share 40% amino acid sequence identity while the subfamilies 70% and all show the same structural architecture. ALDH1A3 belongs to ALDHA subfamily composed of 3 members: 1A1 and 1A3 expressed mainly in brain tissue and 1A2 present in the tissues of the male urogenital system.

To date, on the market, there are several fluorescent tools for the localization of enzymes of the aldehyde dehydrogenase superfamily. However, these molecules are poorly selective and, in any case, directed to other isoforms of the ALDH1A enzyme.

Examples of these molecules are:

pq009118—ALDEFLOUR, non-selective;
oc8b00313—ALDeSense, ALDH1A1-selective;
nihms-1570368—Red ALDeSense, ALDH1A1-selective;
ncomms4662—AldeRed 588-A, non-selective;
cbic.201900771—STA-55, non-selective (tested with ALDH1A1/ALDH3A1);
acscentsci.9b01022—LEI-945, ALDH1A-selective;
acs.bioconjchem. 6b00618—"Probe 5", ALDH3A1 selective.

Curcumin, a compound of natural origin, is widely used in the food industry as a dye (E100) and has a strong fluorescence. Although curcumin has been the subject of numerous studies aimed at identifying its pharmacological profile, its poor solubility and its pleiotropy of action have so far led to the failure of all clinical studies relegating it to mere academic curiosity. Curcumin has a totally different structure with respect to those which have been listed above as directed to enzyme ALDH1A.

SUBJECT AND SUMMARY OF THE INVENTION

Therefore, it is a scope of the present invention to provide new highly specific fluorescent probes, which are selective for the ALDH1A3 isoform, capable of clearly detecting tumour tissue with respect to healthy tissue.

According to the present invention, this scope is achieved by the compound as defined in claim 1 or claim 2.

DETAILED DESCRIPTION OF PREFERRED EMBODIMENTS OF THE INVENTION

Figure 1:
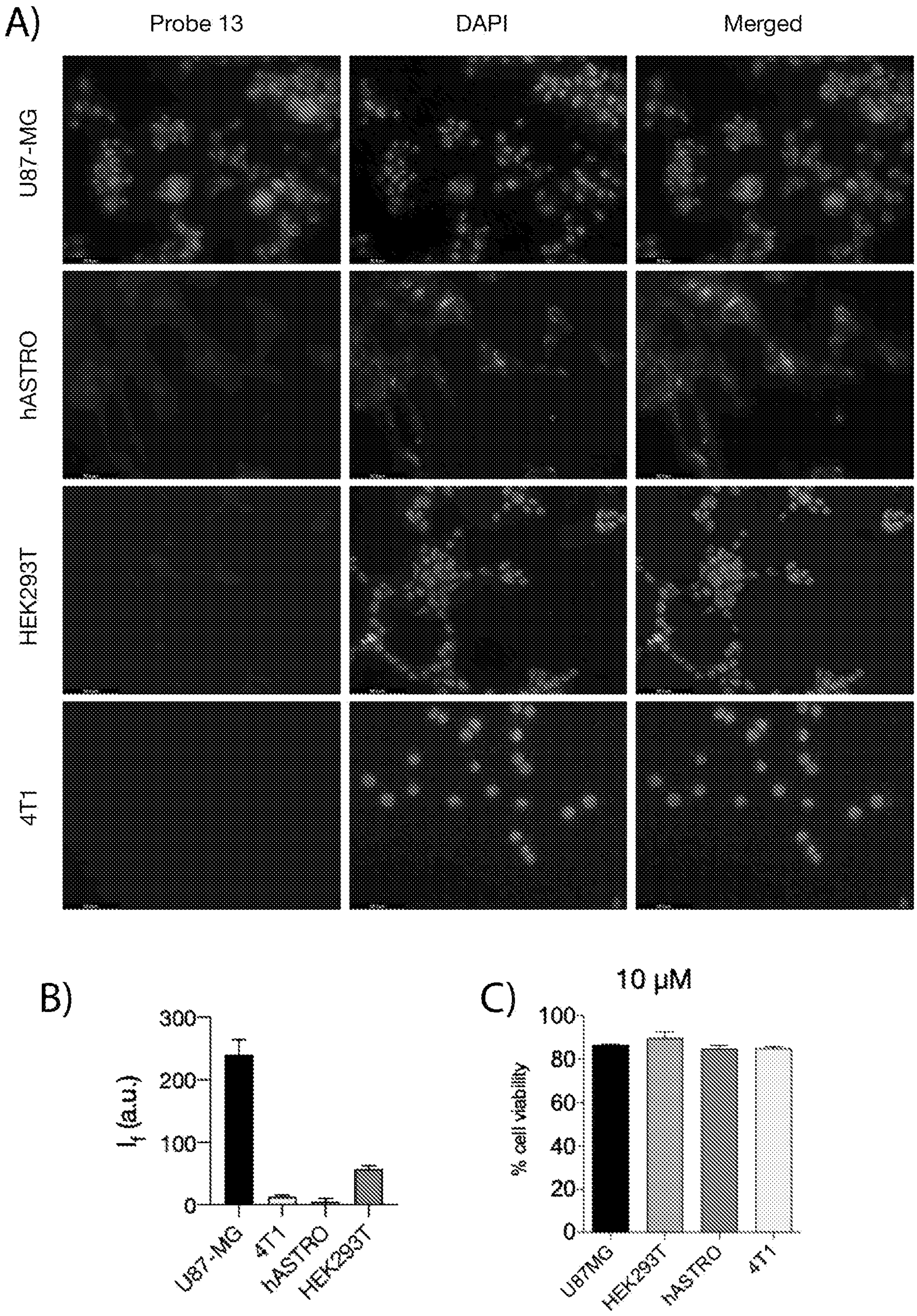
FIG. 1A shows confocal fluorescence microscope images for probe 13 detection in different cell lines at 10 μM.
FIG. 1B shows a graph representing relative fluorescence intensity of the images from FIG. 1A.
FIG. 1C shows a graph representing cell viability at 10 μM of probe 13.

The present invention relates to compounds of formula

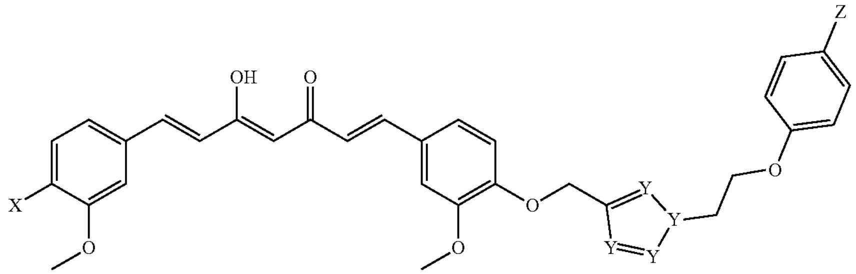

X is —OH, —N $(CH_3)_2$,

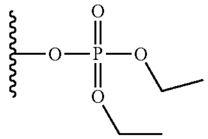 or 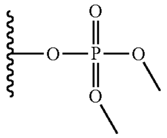 or

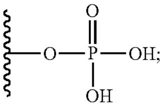

Y is CH or N; and

Z is

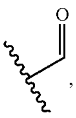, 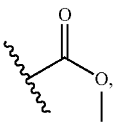 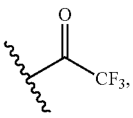 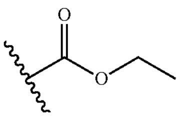 or

-continued
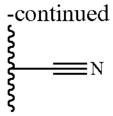
and salts, solvates and solvates of the salts thereof.
The present invention also relates to compounds selected from the group consisting of:
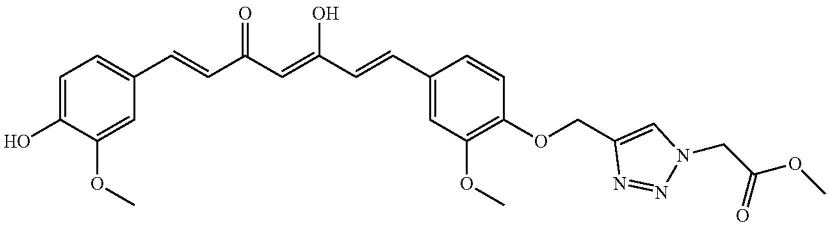
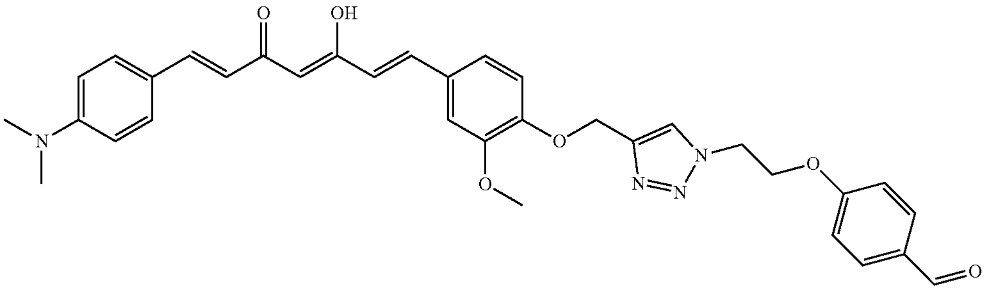
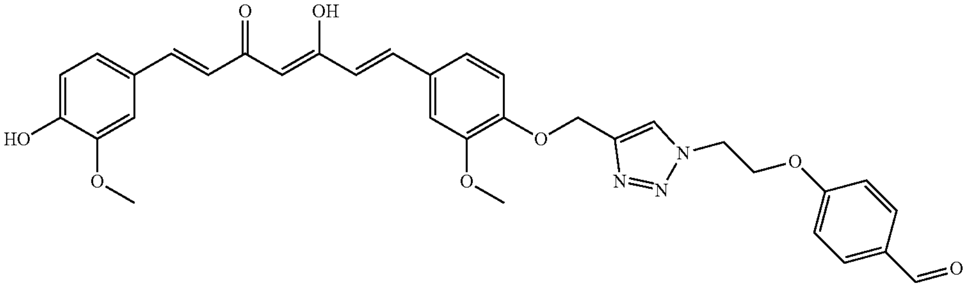
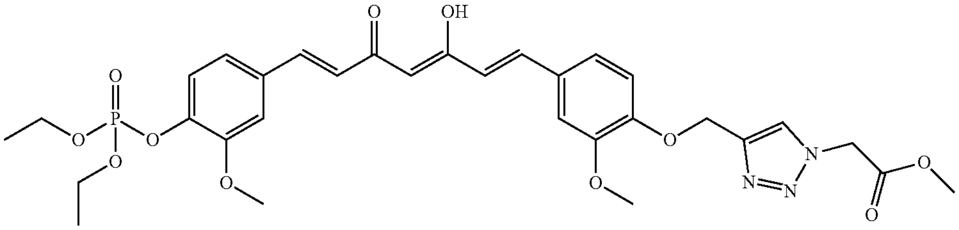
and
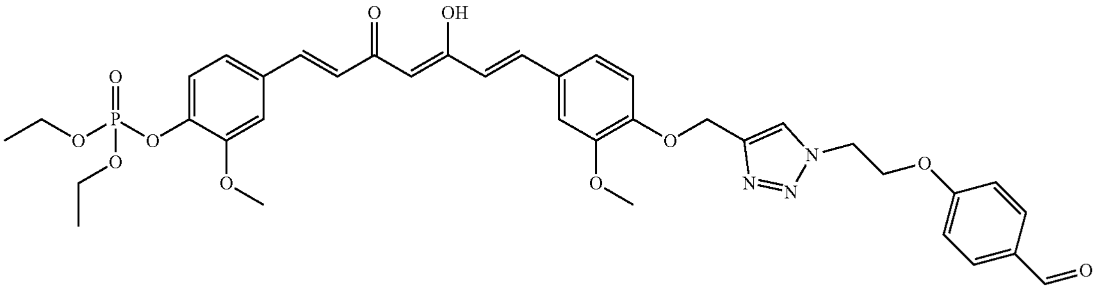

More preferably the compound is

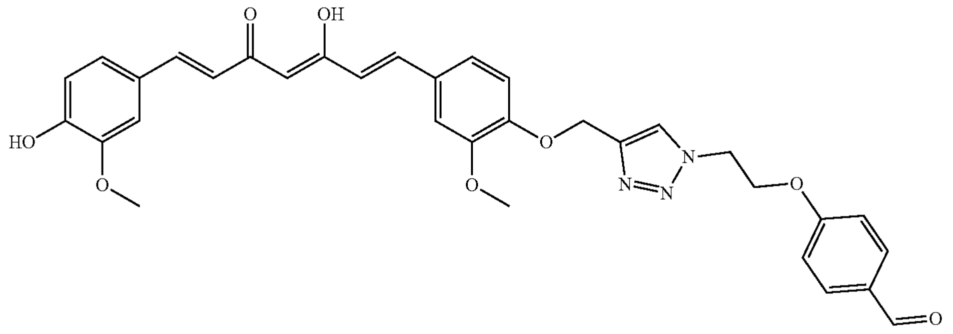 [SMILES: COc1cc(/C=C/C(=O)/C=C(O)/C=C/c2ccc(OCc3cn(CCOc4ccc(C=O)cc4)nn3)c(OC)c2)ccc1O]

The above compounds are fluorescent probes selective for enzyme ALDH1A3.

The above compounds are derived from curcumin which is not used as a pharmacophore, but instead as chromophore exploiting its intrinsic fluorescence, for the identification of cells that express the ALDH1A3 isoform.

In detail, the natural compound was functionalized differently on both phenolic groups with a group able to interact with the biological target and a second group able to modify the emission wavelength and/or to increase the solubility of the final compound and a tail was added that exposed a benzaldehyde group, known to be a non-selective inhibitor of ALDH, or a methyl-ester group, present in some inhibitors known in the literature, through a triazole linker. The scaffold of the natural compound was also modified by inserting phosphate groups and by modifying one of the aromatic portions with a dimethylamine group in order to increase the solubility of the probes, as well as modulating their fluorescence and selectivity towards the various isoforms of ALDH1A.

The present invention also relates to pharmaceutical compositions comprising at least one of the above said compounds.

The above compounds and compositions can be used in the selective detection of enzyme ALDH1A3.

The above compounds and compositions can be used as support for existing treatments, making it possible to obtain molecular tools to be used on patients both for the diagnosis and for the pharmacological treatment of HGG. Furthermore, in virtue of the ability of the above compounds to selectively bind to the ALDH1A3 enzyme, these molecules can be used in neurosurgery for a more accurate and precise resection of glioblastomas during surgery, limiting the onset of any relapses. In particular, they are useful during surgery to precisely identify the tumour mass and totally resect the glioblastoma.

The above compounds or compositions can also be used in diagnosing glioblastomas.

The examples disclosed in detail hereinafter prove the following points.

All 3 enzymes belonging to the subfamily 1A of aldehyde dehydrogenases were expressed recombinantly in bacterial cells and purified to homogeneity. The pure enzymes were then used to study the interaction with the molecules according to the invention, using various in vitro biochemical assays. In particular, the affinity for the isoenzymes of the selected molecules was measured through the use of a TECAN SPARK and a TECAN SUNRISE. Fluorescence assays were performed in the presence of different protein concentrations and the activity assays were conducted by measuring $NAD^+$ consumption. According to their specific activity, all molecules were characterized by values of $K_D$, $K_M$, $K_i$ and $IC_{50}$, showing a net selectivity in specifically binding the ALDH1A3 enzyme. The probes having curcumin and recognizing the ALDH1A3 enzyme were tested in a cellular context, using four different cell lines classified by the presence or absence of the isoform studied: human glioblastoma line (U87MG, ALDH1A3 positive), embryonic kidney cell line (HEK293T, ALDH1A2 positive), human astrocyte line (hAstro, ALDH1A1 positive) and a breast cancer line (4T1, ALDH1A negative). The analysed probes did not determine significant cell mortality in the lines at 24 h showing a viability of 94%, and they were administered to the cell lines and fixed on the slide, to determine their localization and fluorescence. The three negative ALDH1A3 lines did not show fluorescence, highlighting that the probes are unable to bind any other molecule in the cell. On the other hand, the human glioblastoma line U87MG, ALDH1A3 positive, shows a strong fluorescence, localized at the cytoplasmic level. The binding ability of the probes to these cell lines was also verified and confirmed by flow cytometry. All the results obtained show that the compounds (probes) according to the present invention are able to selectively bind to the target enzyme ALDH1A3 and to make the tumour cells that overexpress it fluorescent, highlighting in a very precise way a brain tumour in mouse models, compared to healthy cells.

EXAMPLES

Example 1: Chemical Synthesis of the Compounds

General: NMR spectra were measured on Bruker Avance 400 MHz spectrometer or on a Bruker Avance 500 MHz. Chemical shifts were referenced to the residual solvent signal ($CDCL_3$: $\delta_H$=7.21, $\delta_C$=77.0). Reactions were monitored by thin-layer chromatography (TLC) on Merck 60 F254 (0.25 mm) plates, visualized by staining with 5% $H_2SO_4$ in EtOH and heating. Organic phases were dried with $Na_2SO_4$ before evaporation. Chemical reagents and solvents were purchased from Sigma-Aldrich, TCI Europe or Fluorchem and were used without further purification unless stated otherwise. Petroleum ether with boiling point of 40-60° C. was used. Silica gel 60 (70-230 mesh) was used for gravity column chromatography (GCC).

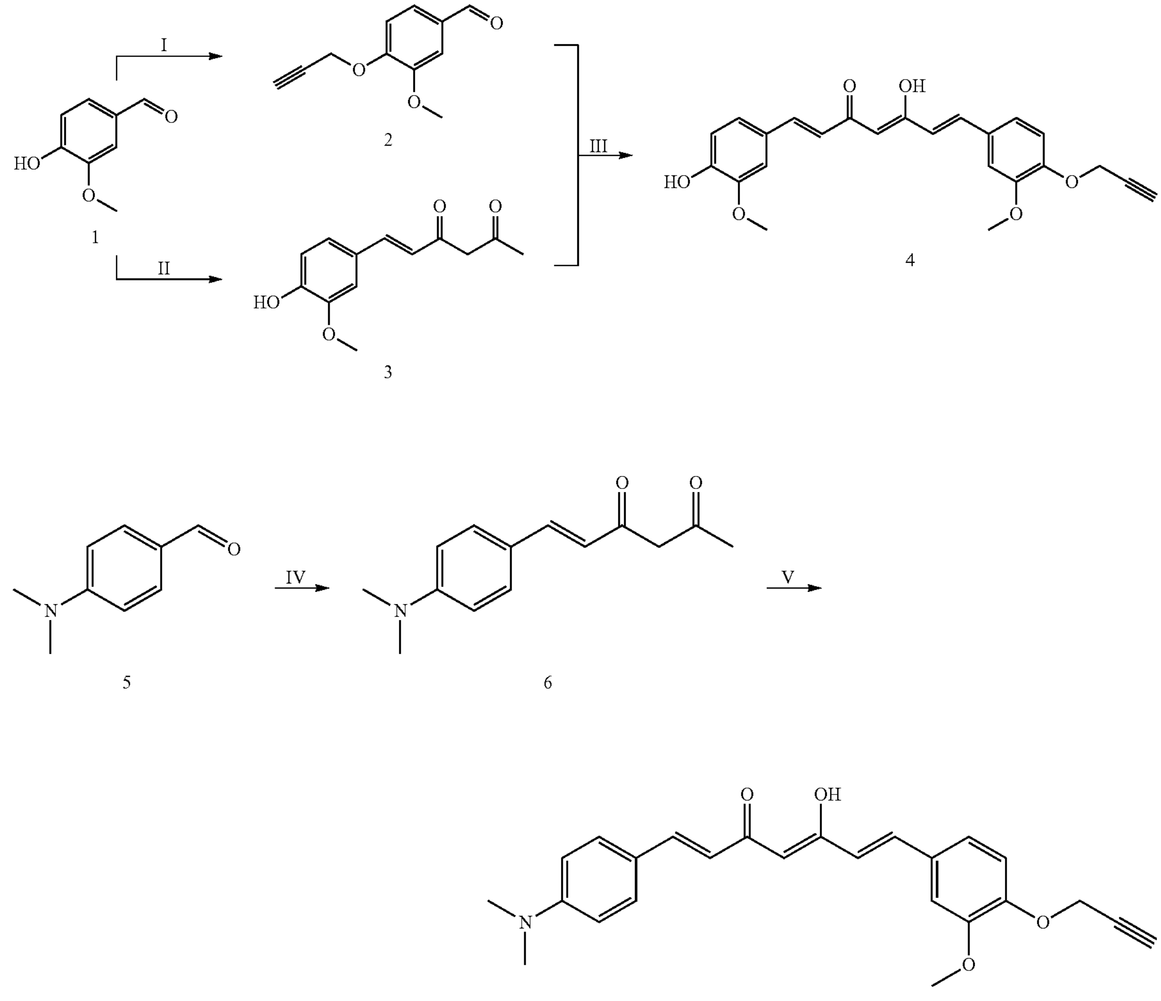

1 2 3 4 5 6 7

Scheme 1. Synthesis of Curcuminoids 4 and 7.

I) $K_2CO_3$, propargyl bromide, acetone reflux; II) acetyl acetone, boron oxide, trimethyl borate, n-butylamine, DMF; III) boron oxide, trimethyl borate, n-butylamine, DMF; IV) acetyl acetone, boron oxide, trimethyl borate, n-butylamine, EtOAc; V) 2, boron oxide, trimethyl borate, n-butylamine, EtOAc.

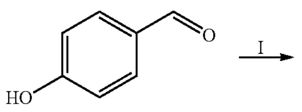

8

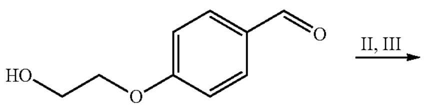

9

-continued

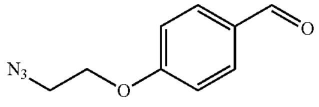

10

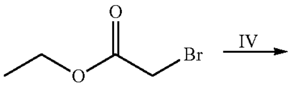

11

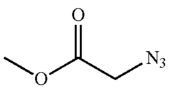

12

Scheme 2. Synthesis of Azide 10 and aPAlkyne 12.

I) $K_2CO_3$, 2-bromoethanol, DMF 80° C.; II) MsCl, TEA, DCM; III) NaN, NaI, DMF, 65° C.; IV) $NaN_3$, DMF, 90° C.

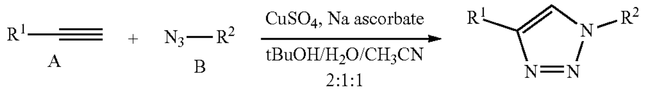
| Compound | A | B | Structure |
|---|---|---|---|
| 13 | 4 | 10 | 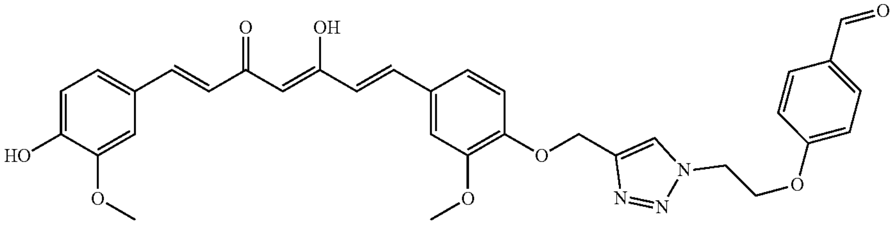 [SMILES: COc1cc(/C=C/C(=O)/C=C(O)/C=C/c2ccc(OCc3cn(CCOc4ccc(C=O)cc4)nn3)c(OC)c2)ccc1O] |
| 14 | 4 | 12 | 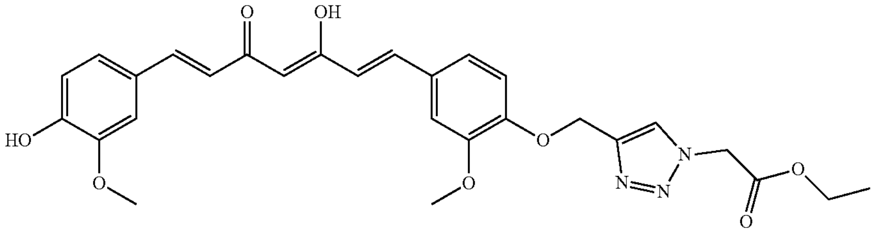 [SMILES: CCOC(=O)Cn1cc(COc2ccc(/C=C/C(O)=C/C(=O)/C=C/c3ccc(O)c(OC)c3)cc2OC)nn1] |
| 15 | 7 | 10 | 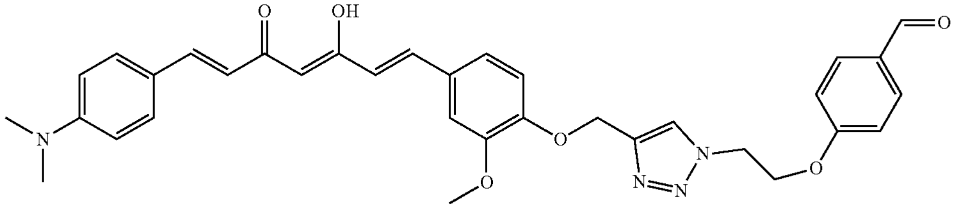 [SMILES: COc1cc(/C=C/C(O)=C/C(=O)/C=C/c2ccc(N(C)C)cc2)ccc1OCc1cn(CCOc2ccc(C=O)cc2)nn1] |
Table 1. Structure and synthesis of probes 13, 14 and 15
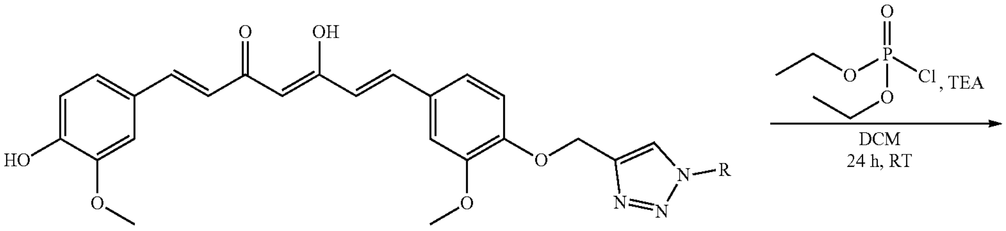
13 R =
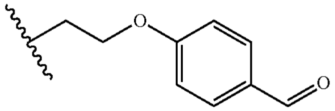
14 R =
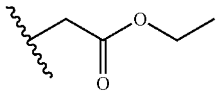

-continued

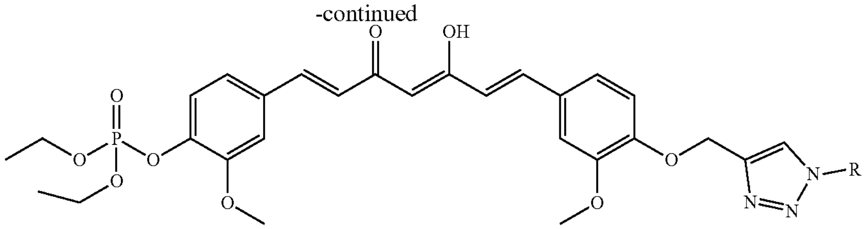

16 R = 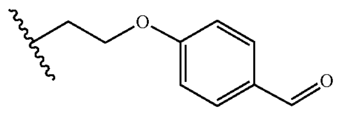

17 R = 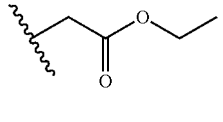

Scheme 3. Synthesis of Probes 16 and 17

3-methoxy-4-propargyloxybenzaldehyde (2)

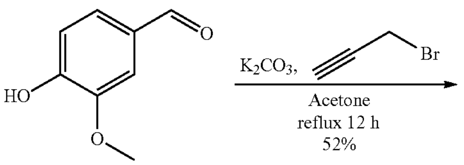

1

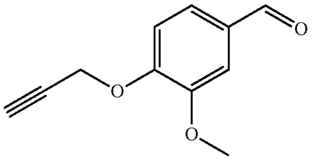

2

Propargyl bromide (6.01 mL, 80% w/v in toluene, 52.580 mmol, 2 eq) was added to a suspension of vanillin (1, 4 g, 26.290 mmol, 1 eq) and potassium carbonate (5.09 g, 36.806 mmol, 1.4 eq) in acetone (80 mL). The suspension was heated to reflux for 12 h and the solvent was removed under reduced pressure. Water was added and the aqueous phase was extracted with EtOAc, washed with water, brine and dried. The crude was purified by column chromatography (PE/EtOAc 9:1 as eluent) to give 3-methoxy-4-propargyloxybenzaldehyde (2, 2.58 g, 52%) as white crystalline solid. $^1$H NMR (400 MHz, CDC13) δ (400 MHz, CDCI3) 9.87 (s, 1H), 7.47 (dd, $J_1$=6.8, J2=1.4 Hz, 1H), 7.44 (d, J=1.4 Hz, 1H), 7.14 (d, J=6.8 Hz, 1H), 4.86 (d, J=2.5 Hz, 2H), 3.95 (s, 3H), 2.56 (t, J=2.5 Hz, 1H). $^{13}$C NMR (100 MHz, $CDCl_3$) δ 190.9, 152.1, 150.0, 130.9, 126.3, 112.5, 109.4, 77.4, 77.2, 56.6, 56.0.

(E)-6-(4-hydroxy-3-methoxyphenyl) hex-5-ene-2,4-dione (3)

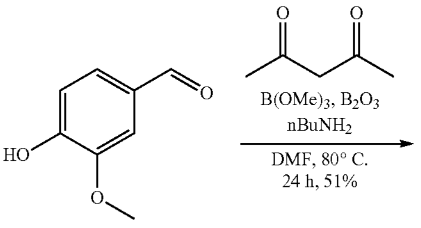

1

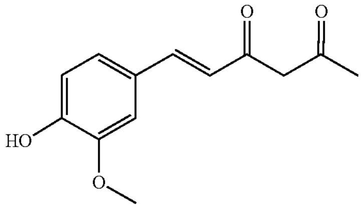

3

Boron oxide (14.6 g, 174.85 mmol, 5.3 eq) and acetyl acetone (13,5 mL, 131.46 mmol, 4 eq) were dissolved in DMF (10 mL) stirred at 80° C. for 1 hour. The mixture was cooled to 0° C., then trimethyl borate (23,8 mL, 209.55 mmol, 6.38 eq) and vanillin (1, 5g, 32.86 mmol, 1 eq) were added. Butylamine (1.3 mL, 13.27 mmol, 0.4 eq) was then added dropwise. The obtained mixture was heated to 80° C. for 24 hours, then cooled to room temperature and 5% $ACOH_{ag}$ (200 mL) was added. The suspension was then stirred for 2 hours at room temperature and a yellow precipitate formed. The precipitate was filtered, washed with water (3×100 mL), and purified by chromatography over silica (PE/EtOAc 7:3) to afford (E)-6-(4-hydroxy-3-methoxyphenyl) hex-5-ene-2, 4-dione (3, 3.22g, 51%) as a yellow solid. 1H NMR (400 MHz, $CDCl_3$) δ (400 MHz, CDCI3) 7.53 (1H, d, J=15.8 Hz, 1H), 7.09 (1H, dd, J=8.2 Hz, J=1.9 Hz, 1H), 7.02 (d, J=1.9 Hz, 1H), 6.92 (d, J=8.2 Hz, 1H), 6.32 (d, J=15.8 Hz, 1H), 5.91 (1H, bs, OH), 5.62 (s, 1H), 3.94 (s, 3H), 2.16 (s, 3H). $^{13}$C NMR (100 MHz, $CDCl_3$) δ 197.0, 177.9, 147.7, 146.7, 140.0, 127.6, 122.6, 120.2, 114.8, 109.5, 100.7, 55.9, 26.5.

(1E, 4Z, 6E)-5-hydroxy-1-(4-hydroxy-3-methoxy-phenyl)-7-(3-methoxy-4-(prop-2-yn-1-yloxy) phenyl) hepta-1, 4, 6-trien-3-one (4)

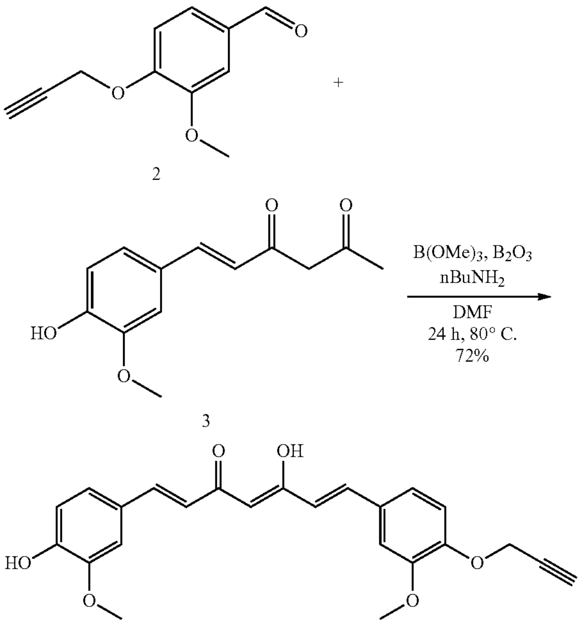

2
3
4

Boron oxide (142 mg, 1.708 mmol, 0.4 eq) and 3 (1 g, 4.269 mmol, 1 eq) were dissolved in DMF (2 mL) stirred at 80° C. for 1 hour. The mixture was cooled to 0° C., then trimethyl borate (810 μL, 7.129 mmol, 1.67 eq) and 2 (893 mg, 4.696 mmol, 1.1 eq) were added. Butylamine (7 μL, 0.071 mmol, 0.17 eq) was then added dropwise. The obtained mixture was heated to 80° C. for 24 hours, then cooled to room temperature and 5% AcOH aq (50 mL) was added. The suspension was then stirred for 2 hours at room temperature and an orange precipitate formed. The precipitate was filtered, washed with water (3×100 mL), and purified by chromatography over silica (PE/EtOAc 6:4) to afford (1E, 4Z, 6E)-5-hydroxy-1-(4-hydroxy-3-methoxy-phenyl)-7-(3-methoxy-4-(prop-2-yn-1-yloxy) phenyl) hepta-1, 4, 6-trien-3-one (4, 1.21 g, 72%) as an orange solid. $^{1}H$ NMR (400 MHz, $CDCl_3$) δ 7.59 (d, J=15.7 Hz, 2H), 7.08-7.12 (m, 3H), 7.04 (s, 2H), 6.92 (d, J=8.2 Hz, 1H), 6.45-6.51 (m, 2H), 5.81 (s, 1H), 4.79 (d, J=2.3 Hz, 2H), 3.92 (d, J=6.2 Hz, 6H), 2.53 (t, J=4.84, 3H).

1-(4-(Dimethylamino)phenyl)-5-hydroxyhexa-1,4-dien-3-one (6)

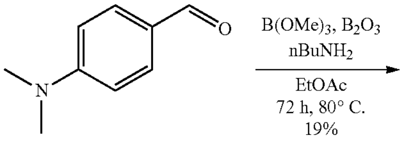

5

-continued

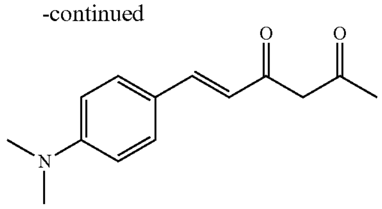
6

Boron oxide (4.17 g, 46.933 mmol, 0.4 eq) and 5 (1 g, 6.705 mmol, 1 eq) were dissolved in EtOAc (50 mL) stirred at 80° C. for 1 hour. The mixture was cooled to 0° C., then trimethyl borate (761 μL, 6.705 mmol, 1 eq) and acetylacetone (6.88 mL, 67.047 mmol, 10 eq) were added. Butylamine (665 μL, 6.705 mmol, 1 eq) was then added dropwise. The obtained mixture was heated to 80° C. for 72 hours, then cooled to room temperature. $H_2SO_4$ 2M (50 mL) was added, then the organic phase was washed with NaHCO3 s.s. (50 mL), water, brine and dried. The crude was purified by column chromatography (PE/EtOAc 9:1 as eluent) to afford 1-(4-(Dimethylamino)phenyl)-5-hydroxyhexa-1, 4-dien-3-one (6, 291 mg, 19% yield) as a red powder. $^{1}H$ NMR (400 MHz, $CDCl_3$) δ 7.38 (s, 1H), 7.30 (d, J=9.3 Hz, 2H), 6.64 (d, J=9.3 Hz, 2H), 3.04 (s, 6H), 1.90 (d, J=5.7 Hz, 6H).

(1E,4Z, 6E)-1-(4-(dimethylamino) phenyl)-5-hydroxy-7-(3-methoxy-4-(prop-2-yn-1-yloxy)phenyl) hepta-1,4, 6-trien-3-one (7)

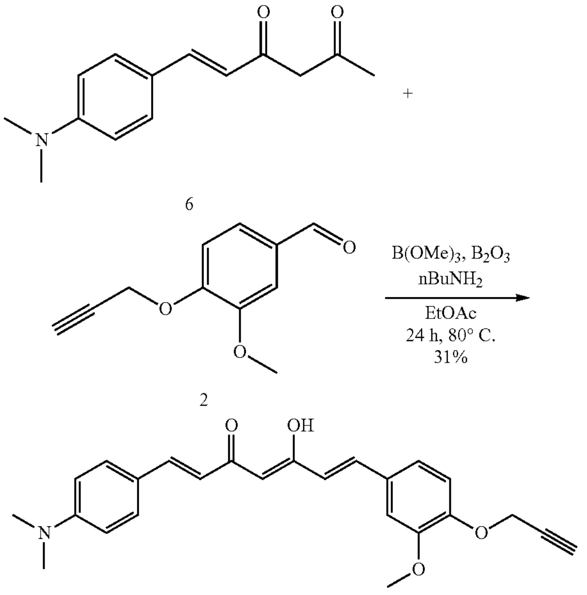

6
2
7

Boron oxide (17 mg, 0.223 mmol, 0.4 eq) and 6 (130 mg, 0.558 mmol, 1 eq) were dissolved in EtOAc (3 mL) stirred at 80° C. for 1 hour. The mixture was cooled to 0° C., then trimethyl borate (191 μL, 0.949 mmol, 1.67 eq) and 2 (106, 0.558 mmol, 1 eq) were added. Butylamine (9 μL, 0.095 mmol, 0.17 eq) was then added dropwise. The obtained mixture was heated to 80° C. for 24 hours, then cooled to room temperature. $H_2SO_4$ 2M (50 mL) was added, then the organic phase was washed with water, brine and dried. The crude was purified by column chromatography (PE/EtOAc 7:3 as eluent) to afford (1E, 4Z, 6E)-1-(4-(dimethylamino) phenyl)-5-hydroxy-7-(3-methoxy-4-(prop-2-yn-1-yloxy) phenyl) hepta-1, 4, 6-trien-3-one (7, 70 mg, 19% yield) as a red powder. $^{1}H$ NMR (300 MHz, $CDCl_3$) δ 7.63 (d, J=15.8 Hz, 1H), 7.57 (d, J=15.8 Hz, 1H), 7.46 (d, J=8.9 Hz, 2H), 7.08 (m, 3H), 6.69 (d, J=8.6 Hz, 2H), 6.50 (d, J=15.8 Hz, 1H), 6.43 (d, J=15.8 Hz, 1H), 5.78 (s, 1H), 4.80 (d, J=2.4 Hz, 2H), 3.92 (s, 3H), 3.03 (s, 6H), 2.53 (t, J=2.3 Hz, 1H).

4-(2-Hydroxyethoxy) benzaldehyde (9)

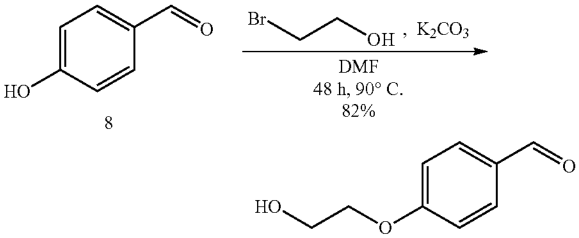

8

9

To a stirred solution of 4-hydroxybenzaldehyde (8, 1 g, 8.188 mmol, 1 eq) in DMF (10 mL) $K_2CO_3$ (2.26 g, 16.376 mmol, 2 eq) and 2-bromoethanol (1.16 mL, 16.376 mmol, 2 eq) were added. The reaction was heated at 90° C. for 48 hours, then cooled to room temperature. $H_2SO_4$ 2M (20 mL) was added, then the mixture was extracted with PE/$Et_2O$ 3:1 (50 mL) and the organic phase was washed with water, brine and dried. The crude was purified by column chromatography (PE/EtOAc 5:5 as eluent) to afford 4-(2-Hydroxyethoxy) benzaldehyde (9, 1.36 g, 100%) as a colorless oil. $^{1}H$ NMR (400 MHz, $CDCl_3$) δ 9.90 (s, 1H), 7.85 (d, J=9.3 Hz, 2H), 7.03 (d, J=8.7 Hz, 2H), 4.18 (t, J=9.0 Hz, 2H), 4.02 (q, J=9.3 Hz, 2H).

4-(2-Azidoethoxy) benzaldehyde (10)

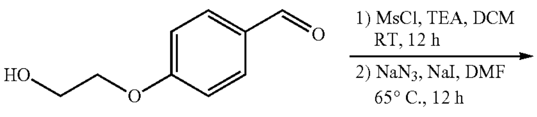

9

-continued

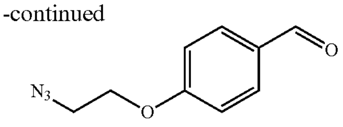

10

To a stirred solution of 9 (680 mg, 4.094 mmol, 1 eq) in DCM (10 mL), TEA (628 μL, 4.503 mmol, 1.1 eq) and methansulfonyl chloride (350 μL, 4.503 mmol, 1.1 eq) were added. The reaction was left at room temperature for 12 hours, then quenched with $H_2SO_4$ 2M (20 mL). The organic phase was then washed with water, brine and dried. The crude was dissolved in DMF (10 mL), then sodium azide (798 mg, 12.382 mmol, 3 eq) and a catalytic amount of NaI were added. The reaction was heated at 65° C. for 12 hours, then quenched with brine. The organic phase was dried, and the crude was purified by column chromatography (PE/EtOAc 5:5 as eluent) to afford 4-(2-Azidoethoxy) benzaldehyde (10, 712 mg, 91%) as a yellow oil. $^{1}H$ NMR (400 MHz, $CDCl_3$) δ=3.66 (t, J=4.9 Hz, 2H), 4.23 (t, J=4.9 Hz, 2H), 7.04 (d, J=8.8 Hz, 2H), 7.85 (d, J=8.8 Hz, 2H), 9.91 (s, 1H). $^{13}C$ NMR (100 MHz, $CDCl_3$) δ=50.0, 67.2, 114.8, 130.5, 132.0, 163.1, 190.7.

Ethyl 2-azidoacetate (12)

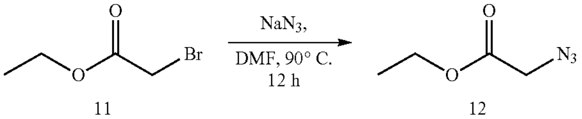

11

12

To a stirred solution of ethyl 2-bromoacetate (11, 1 mL, 9.017 mmol, 1 eq) in in DMF (10 mL), sodium azide (1.759 mg, 27.052 mmol, 3 eq) was added. The reaction was heated at 90° C. for 12 hours, then quenched with brine and extracted with PE. The organic phase was dried, and concentration of the solvent under reduced pressure gave ethyl 2-azidoacetate (12, 1.16 g, 100%) as a colorless oil. $^{1}H$ NMR (400 MHz, $CDCl_3$): δ 4.15 (q, J=6.8 Hz, 2H), 3.77 (d, J=1.2 Hz, 2H), 1.20 (td, J1=7.2, J2=1.2 Hz, 3H). $^{13}C$ NMR (100 MHz, $CDCl_3$): δ 168.1, 61.5, 50.0, 13.8.

General Procedure for Copper Catalyzed 1, 3-Dipolar Cycloaddition: Synthesis of Probe 13 as Example

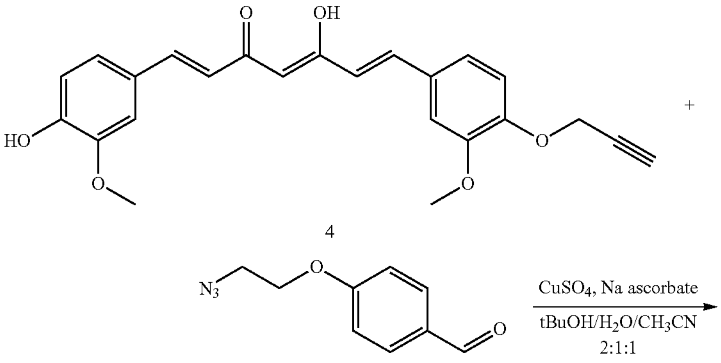

4

10

-continued

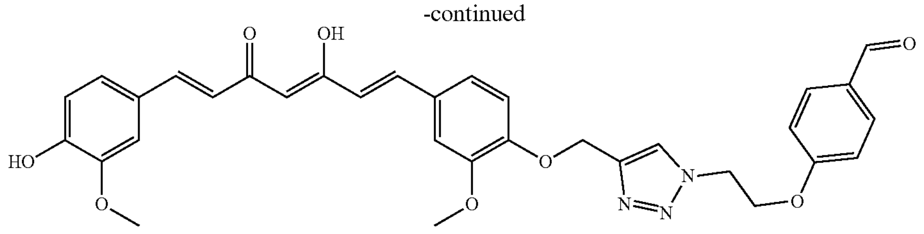

13

To a stirred solution of 4 (50 mg, 0.123 mmol, 1 eq) in t-BuOH/$H_2O$/$CH_3CN$ 2:1:1, 10 (56 mg, 0.256 mmol, 2 eq) and a catalytic amount of $CuSO_4$ and sodium ascorbate were added. The solution was stirred at room temperature for 24 hours, then diluted with brine and extracted with EtOAc. The organic phase was dried and evaporated, then the crude was purified by chromatography over silica gel (PE: EtOAc 3:7 as solvent) to afford 13 (32 mg, 30%) as an orange solid.

13: orange powder, 30%. $^1$H NMR (400 MHz, $CDCl_3$) δ=9.91 (s, 1H), 7.87-7.83 (m, 3H), 7.63 (d, J=10.4 Hz, 1H), 7.59 (d, J=10.4 Hz, 1H), 7.16-7.07 (m, 4H), 6.98-6.92 (m, 3H), 6.51 (dd, $J_1$=15.8 Hz, $J_2$=2.9 Hz, 2H), 5.84 (s, 1H), 5.37 (s, 2H), 4.83 (t, J=4.7 Hz, 2H), 4.48 (t, J=4.7 Hz, 2H), 3.07 (s, 3H), 2.55 (s, 3H). $^{13}$C NMR (100 MHz, $CDCl_3$) δ 190.6, 183.6, 182.7, 162.5, 149.6, 149.3, 147.9, 146.8, 144.0, 140.7, 140.0, 132.0, 130.8, 128.9, 127.6, 124.3, 122.9, 122.5, 122.1, 121.7, 114.8, 114.7, 113.7, 110.4, 109.6, 101.3, 66.4, 62.8, 55.9, 49.7.

14: brown powder. $^1$H NMR (400 MHz, $CDCl_3$) δ =7.83 (s, 1H), 7.60 (dd, $J_1$=15.7 Hz, $J_2$=4.5 Hz, 2H), 7.14-7.07 (m, 4H), 6.95 (d, J=8.2 Hz, 1H), 6.50 (dd, $J_1$=15.7 Hz, $J_2$=2.8 Hz, 2H), 5.83 (s, 1H), 5.38 (s, 2H), 5,17 (s, 2H), 4.28 (q, J=7.1, 2H), 3.69 (s, 3H), 3.92 (s, 3H), 1.31 (t, J=7.1 Hz, 3H). $^{13}$C NMR (100 MHz, $CDCl_3$) δ 183.6, 182.9, 166.0, 149.6, 149.4, 147.9, 146.8, 144.2, 140.7, 140.1, 128.9, 127.6, 124.5, 124.5, 122.9, 122.4, 122.3, 121.7, 114.8, 113.8, 110.5, 109.6, 101.3, 62.8, 62.5, 55.9, 51.0, 14.0.

15: red powder, 31%. $^1$H NMR (400 MHz, $CDCl_3$) δ=9.91 (s, 1H), 7.84-7.86 (m, 2H), 7.67-7.58 (m, 3H), 7.20-7.03 (m, 3H), 6.97 (d, J=8.7 Hz, 2H), 6.57 (d, J=15.8 Hz, 2H), 6.52 (d, J=15.8 Hz, 2H), 5.85 (s, 1H), 5.37 (s, 1H), 4.83 (t, J=4.9 Hz, 2H), 4.48 (t, J=4.9 Hz, 2H), 2.33 (s, 3H), 4.24 (s, 6H). $^{13}$C NMR (100 MHz, $CDCl_3$) δ 190.64, 185.34, 162.51, 149.71, 144.02, 141.35, 137.20, 132.06, 130.81, 129.76, 128.60, 124.27, 122.55, 122.44, 121.24, 114.75, 113.74, 110.51, 102.14, 66.49, 62.89, 56.03, 49.67, 46.46, 29.71.

General Procedure for Diethylphosphate Derivative: Synthesis of Probe 16 as Example

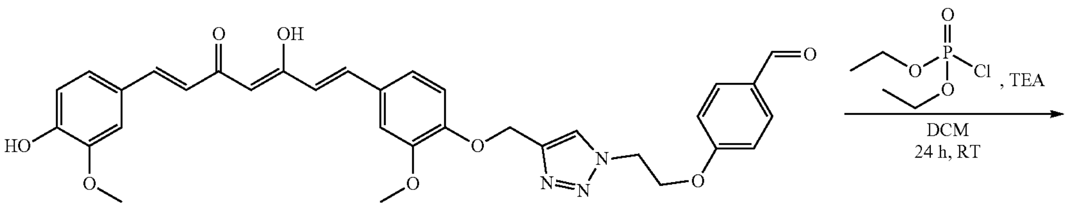

13

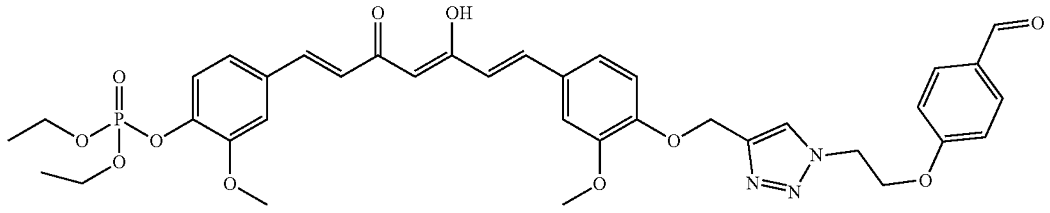

16

To stirred solution of 13 (150 mg, 0.251 mmol, 1 eq) in dry DCM (10 mL), TEA (105 μL, 0.753 mmol, 3 eq) and diethylchlorophosphate (54 μL, 0.377 mmol, 1.5 eq) were added. The reaction was stirred at room temperature for 24 hours, then quenched with $H_2SO_4$ 2M. The organic phase was then washed with brine and dried. The crude was purified by chromatography over silica (EtOAc as eluent) to afford probe 16 (47 mg, 23%) as orange solid.

16: orange amorphous solid, 23%. $^1$H NMR (400 MHz, $CDCl_3$) δ=9.90 (s, 1H), 7.83-7.79 (m, 3H), 7.61 (d, J=15.7 Hz, 2H), 7.35-6.95 (m, 7H), 6.54 (m, 2H), 5.86 (s, 1H), 5.37 (s, 2H), 4.83 (bt, 2H), 4.47 (bt, 2H), 4.30 (m, 4H) 3.95 (s, 3H), 3.93 (s, 3H), 1.39 (t, J=6.89 Hz, 6H). $^{13}$C NMR (100 MHz, $CDCl_3$) δ 190.6, 183.9, 182.3, 162.5, 150.9, 150.9, 149.6, 149.4, 143.9, 141.3, 140.5, 139.5, 132.8, 132.0, 130.7, 128.8, 124.3, 124.0, 122.5, 122.3, 121.6, 121.1, 114.7, 113.7, 111.7, 110.5, 101.6, 66.4, 64.7, 64.7, 62.8, 56.0, 49.7, 16.1, 16.0.

17: brown amorpohus solid, 76%. $^1$H NMR (400 MHz, $CDCl_3$) δ 7.83 (s, 1H), 7.61 (d, J=6.7 Hz, 1H), 7.57 (d, J=6.7 Hz, 1H), 7.32 (d, J=7.9 Hz, 1H), 7.13-7.08 (m, 4H), 6.57-6.49 (m, 2H), 5.85 (s, 3H), 5.36 (s, 2H), 5.16 (s, 2H), 4.30-4.19 (m, 6H), 3.92 (s, 3H), 3.91 (s, 3H), 1.38 (t, J=7.0 Hz, 3H). 1.30 (t, J=7.0 Hz, 3H). $^{13}$C NMR (100 MHz, $CDCl_3$) δ 184.0, 182.2, 166.0, 150.8, 149.7, 149.5, 144.1, 141.3, 140.6, 139.4, 132.8, 128.7, 124.6, 124.0, 122.3, 121.5, 121.0, 113.7, 111.7, 110.5, 101.6, 64.7, 62.8, 62.5, 56.0, 51.0, 29.7, 16.1, 14.0.

Obtained result. A library of 3 fluorescent compounds to test for potency and selectivity towards the identified target enzyme, ALDH1A3

Example 2: Expression and Purification of Human ALDHs

A common protocol to express and purify all three members of the ALDH1A subfamily has been optimized. Briefly, induced cells, collected by centrifugation, were re-suspended in an appropriate volume of lysis buffer (50 mM $Na_2HPO_4$, 300 mM NaCl, 1 mM β-mercaptoethanol, 20 mM imidazole, pH 7.5) added of benzonase nuclease (250 U/μL) and Protease inhibitor cocktail from SIGMA. After ultracentrifugation, the clarified sample was purified by a His-tag affinity chromatography followed by size-exclusion chromatography, using an AKTA FPLC system, at 4° C. To evaluate the purity and homogeneity of the protein, after each purification step, eluted d fractions were analyzed by SDS-PAGE and the protein quantification was always determined by Bradford protein assay.

Result

This procedure allowed us to obtain about 20 mg of pure and active human ALDH1A3, ALDH1A2 and ALDH1A1 used for all crystallization trials and kinetic analyses.

Example 3. Biochemical Analysis to Calculate Enzyme Kinetic Values of the Fluorescent Compounds

Experiment 1

All five compounds were dissolved in DMSO (100%) to obtain two different initial stocks, one at 10 mM and a second one at 1 mM. We performed different screening for the solubility in our assay buffer, composed by 20 mM Tris HCl pH=8, 150 mM KCl, 1 mM B-mercaptoethanol, 500 uM NAD+. The assay can be executed at a maximum DMSO percentage of 15%. The maximum probe concentration tested was 500 uM—15% DMSO. All the compounds were tested using a Tecan—SPARK, to analyze their absorbance, excitation and emission wavelength. Based on the literature, the absorbance of the curcumin by itself is comprised between 420 and 425 nm. At first, we measured the absorbance, and from those values, we performed a 3D analysis to highlights the correct Ex and Em wavelengths. To avoid any possible background in the fluorescence signal we performed a screening of every possible buffer used in our assays.

Result

With none of them we obtain any significant increase in the intrinsic fluorescence, while we observed a significant positive increment in complex with the three isoenzymes, in particular with ALDH1A3 for probe 13 and 14 and no good result were obtained for probe 15 and 16.

Experiment 2

To determine the possible interactions with the recombinant enzymes ALDH1A1, ALDH1A2 and ALDH1A3, we calculate the $K_D$, the $K_M$, the $IC_{50}$ and the $K_i$ values for all five compounds.

$IC_{50}$ evaluation: on a Tecan—SUNRISE, probe 13 was tested in a serial dilution series from 200 μM to 3, 125 μM, against all the three isoenzymes. The recipe of reaction buffer was: 20 mM Tris HCl pH=8, 150 mM KCl, 1 mM B-mercaptoethanol, 500 μM $NAD^+$, 15% DMSO fixed, 20 mM acetaldehyde and 2.7 μM each isoenzyme. The analysis was conducted measuring the NADH formation, that has a specific absorbance wavelength (340 nm). The test was performed in triplicate with all the three isoenzymes.

$K_i$ evaluation: on a Tecan—SUNRISE, probe 13 was tested as a possible competitive inhibitor, at a variable concentration (200, 100, 50, 10, 1 and 0 μM). In the same plate, different the acetaldehyde was tested at concentrations (1, 2.5, 5, 10, 15 and 20 mM) to describe the competitive mechanism. The recipe of the buffer reaction was the same as described before. The analysis was conducted measuring the NADH formation, that has a specific absorbance wavelength (340 nm). The test was performed in triplicate only with the ALDH1A3.

$K_D$ evaluation: on a Tecan—SPARK, probe 14 and 13 were tested at a fixed concentration of 10 μM. All the isoenzymes were tested in wide range of concentrations (from 100 μM to 1 μM). The analysis was settled with a BW of 20, monitoring the Em wavelength in range comprised between 520 and 535 nm for probe 14 and 520 and 580 nm for probe 13. The Ex was fixed at 420 nm for probe 14 and 440 nm for probe 13. The test was performed in quadruplicate with all the three isoenzymes. The recipe of the buffer reaction was the same as described before.

$K_M$ evaluation: on a Tecan—SUNRISE, due to the inconsistency of result of the KD evaluation with probe 13 and to its chemistry nature (benzaldehyde), we performed an analysis to evaluate this compound possible substrate. The compound was tested in a serial dilution from 300 to 3.125 μM, at 5% DMSO. The analysis was conducted measuring the NADH formation, that has a specific absorbance wavelength (340 nm). The recipe of the buffer reaction was the same as described before. The assay was performed only for ALDH1A1 and ALDH1A2. The test was performed in triplicate with all the three isoenzymes.

Result 2

In the table summarises all the results obtained that clearly show that the probe 13 is the most promising fluorescent molecule both for potency and selectivity versus ALDH1A3:

| Compound 13 | $IC_{50}$ | $K_i$ | $K_D$ | $K_M$ |
|---|---|---|---|---|
| ALDH1A1 | 195.8 | / | 31.1 | 255.2 |
| ALDH1A2 | 131.1 | / | 36.9 | 220.0 |
| ALDH1A3 | 1.5 | 0.9 | 38.2 | / |

| | $IC_{50}$ | $K_i$ | $K_d$ | $K_M$ |
|---|---|---|---|---|
| Compound 14 | | | | |
| ALDH1A1 | 114.3 | / | 42.4 | / |
| ALDH1A2 | 92.8 | / | 124.8 | / |
| ALDH1A3 | 14.5 | / | 84.3 | / |
| Compound 15 | | | | |
| ALDH1A1 | 28.5 | / | 23.9 | / |
| ALDH1A2 | N.I. | / | 8.7 | / |
| ALDH1A3 | 5.1 | | 20.4 | / |
| Compound 16 | | | | |
| ALDH1A1 | 149.9 | / | / | / |
| ALDH1A2 | N.I. | / | / | / |
| ALDH1A3 | 8.5 | / | 55.7 | / |
| Compound 17 | | | | |
| ALDH1A1 | 70.1 | / | 18.1 | / |
| ALDH1A2 | N.I. | / | / | / |
| ALDH1A3 | 157.5 | / | 14.9 | / |

N.I. = not inhibited
All the values are expressed in uM.
Standard errors of the mean (SEMs) ≤ 10%.

Example 4: Determination of Selectivity of Probe 13 in Cells and in Vivo Animal Models

Experiment 1

Human U87MG glioblastoma were used as ALDH1A3+ cell lines, HEK293T as ALDH1A2+ cell line, human foetal astrocytes (hASTRO) as ALDH1A1+ cell line and 4T1 mammary carcinoma as triple negative ALDHIA subfamily (checked with Western Blot analysis and RT-PCR). All these cell lines were incubated with Probe 14 and 13 at different concentrations (from 10 μM to 100 nM). At all these concentrations we observed a selectivity of probe 14 and 13 on U87MG cells after 2 h, that appeared to be cytoplasmic, no signal has been verified in HEK293T, hASTRO and 4T1 cell lines. Moreover, we incubated the two probes with cells and analyzed with FACS and we observed a significant positivity in U87MG cells, too.

Result 1

The best selected fluorescent molecule (probe 13) is able to selectively illuminate cells expressing only ALDH1A3 and no other cell types that express other ALDH isoenzymes as show in the FIGS. 1A and 1B.

Experiment 2

We used in vitro and in vivo cells from a mouse high grade glioma cell line, GL261, Briefly, twenty-four 2- to 3-month-old female C57BIC mice were stereotactically implanted under deep general anesthesia (isoflurane supplemented with nitrous oxide) with 1×10 5 GL261 glioblastoma cells. The cells were stereotactically inoculated through a burr hole by a Hamilton syringe into the left striatum (coordinates: 1 mm anteroposterior and 1 mm lateral from bregma, at a depth of 3 mm). All experimental procedures were conducted in accordance with the European Communities Council Directive of 24 Nov. 1986 (86/609 EEC), Recommendation 18/06/2007, Dir. 2010/63/UE, and the Italian law for care and use of experimental animals (DL116/92) and were approved by the Italian Ministry of Health (prot. E669C.15) and the Bioethical Committee of the University of Turin. All animals were housed under a 12-hour light-dark cycle in an environmentally controlled room. All experiments were designed to minimize the numbers of animals used and their discomfort. In each experiment, animals with tumors were allocated to two groups and i.p. injected with probe 14 or probe 13. All drugs were administered intraperitoneally, and treatments were started days 6 after tumor implantation. Animals were euthanized 6 hours after i.p injection. Briefly, they were transcardially perfused under deep anesthesia (ketamine 100 mg/mg, Ketavet, Bayern, Leverkusen, Germany; xylazine 5 mg/kg, Rompun, Bayern, Leverkusen, Germany) with 4% paraformaldehyde in 0.12M phosphate buffer, pH 7.2 to 7.4. The brains were dissected and cut in 50 μm-thick cryostat coronal sections. Sections were incubated were counterstained with 4', 6-diamidino-2-phenylindole (DAPI). After processing, sections were mounted on microscope slides with Tris-glycerol supplemented with 10% Mowiol (Calbiochem). Quantitative and phenotypic evaluations were made on images acquired with a Leica TCS SP5 confocal microscope.

Result 2

Figure 2:
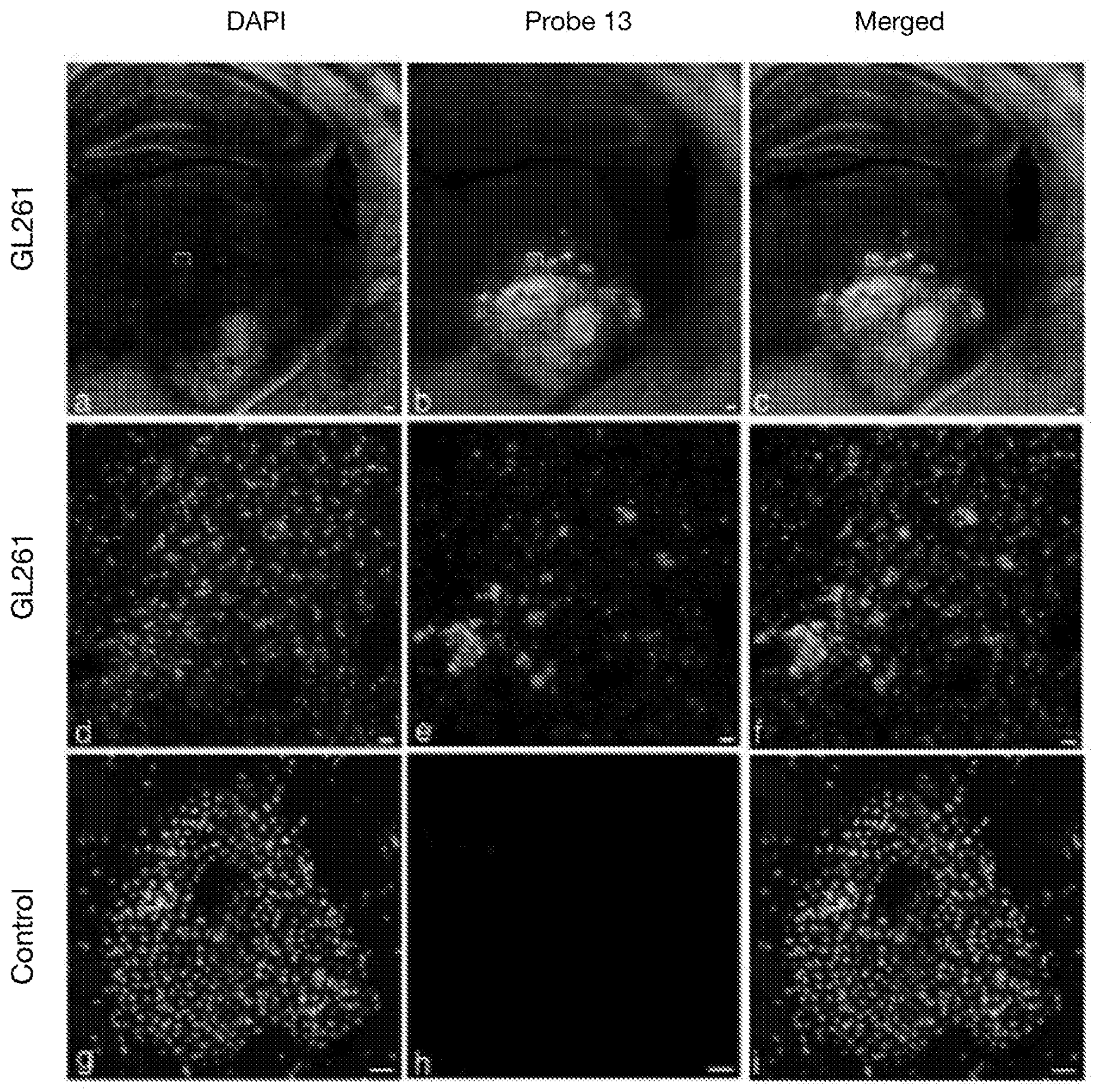
FIG. 2 shows confocal images of: a) cell nuclei stained by DAPI; b) GL261 cells containing probe 13 (in green); c) double fluorescence of DAPI and probe 13; d), e) and f) higher magnification of the area boxed in fig. a), b) and c); g), h) and i) the same coronal section under different fluorescence conditions of a tumor-bearing brain in an animal i.p. injected with compound 14.

As shown in FIG. 2, GL261 glioma cells grow and infiltrate the host brain 6 days after the initial inoculum. a), b) and c) show confocal images showing under different fluorescence conditions the same coronal section of a tumor-bearing brain in an animal i.p. injected with compound 13. In all images the area boxed is the same and it is shown at higher magnification in figure d), e) and f). More in detail: a) Cell nuclei are stained by DAPI. b) GL261 cells containing probe 13 fluoresce in green. Most of the fluorescence comes from glioma cells growing in the left striatum and adjacent structures that have taken up and metabolized probe 13. Scale bars: 25 μM. c) Confocal image showing double fluorescence of DAPI and probe 13. d, e and f) Confocal images showing at higher magnification the area boxed in fig. a, b and c. Fluorescence of probe 13 is mostly contained in the cytoplasm. Scale bars: 25 μM. g, h and i) Confocal images showing under different fluorescence conditions the same coronal section of a tumor-bearing brain in an animal i.p. injected with compound 14 that does not penetrate to any appreciable level in the tumor cells in vivo despite it penetrates GL261 cells in vitro. Scale bars: 25 μM. i) Confocal image under excitation and filtering conditions appropriate both for DAPI and probe 14, no fluorescence due to probe 14 is visible despite the abundance of tumor cells.

In summary, the above examples show that the synthesised compounds are highly specific and selective towards the ALDH1A3 isoform and allow to clearly detect tumour tissue with respect to healthy tissue both ex-vivo on human glioblastoma cells and in vivo in mouse models.

The invention claimed is:
1. A compound of formula
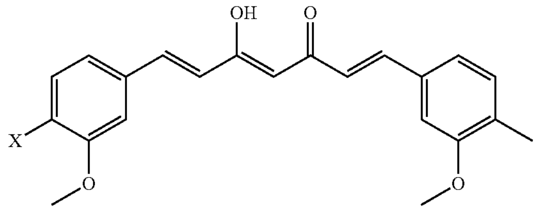
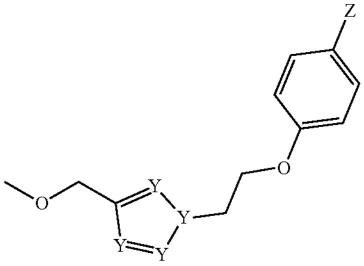
wherein
X is —OH, —$N(CH_3)_2$,
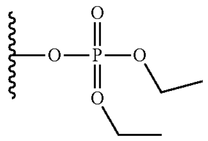
,
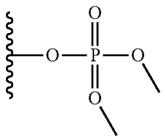
, or
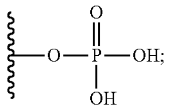
Y is CH or N; and
Z is
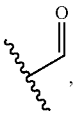
,
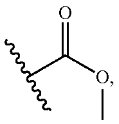
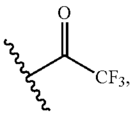
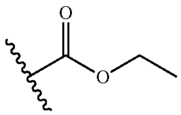
or
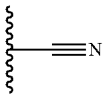
and salts, solvates and solvates of the salts thereof.
2. A compound selected from the group consisting of:
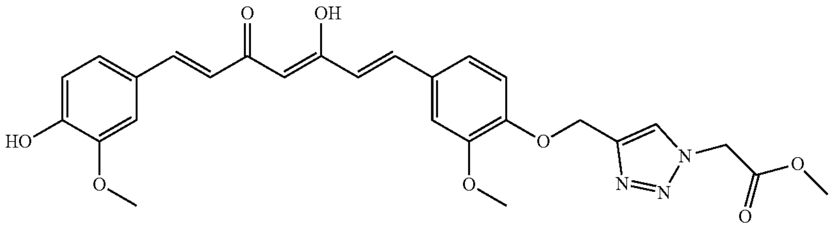
,
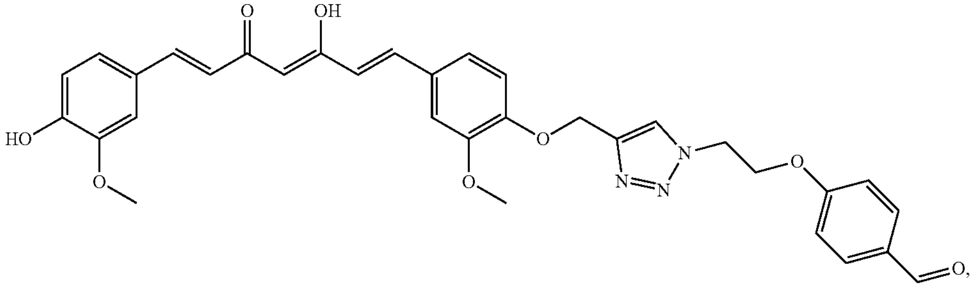
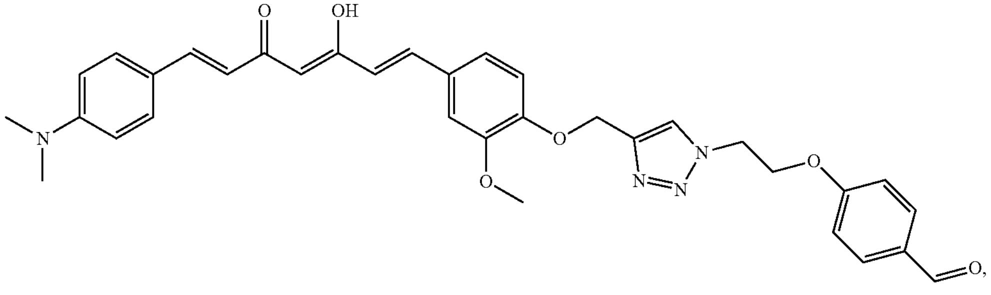

-continued

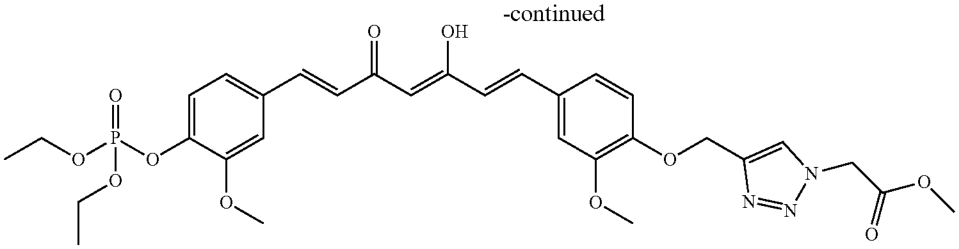

, and

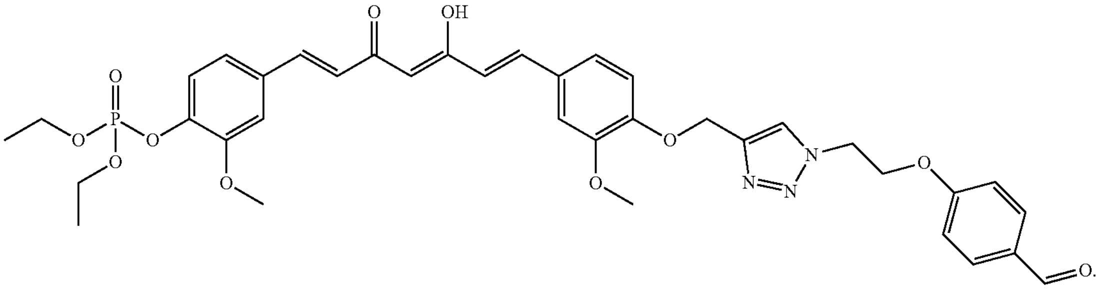

3. The compound according to claim 2 having formula

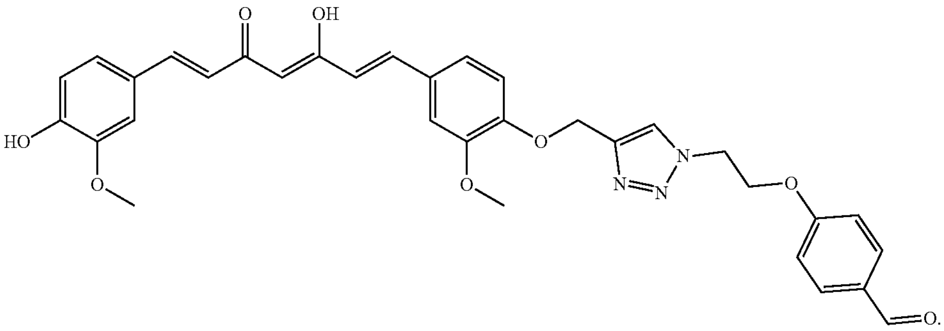 [SMILES: COc1cc(/C=C/C(=O)/C=C(O)/C=C/c2ccc(OCc3cn(CCOc4ccc(C=O)cc4)nn3)c(OC)c2)ccc1O]

4. The compound according to claim 1, wherein the compound is a fluorescent probe selective for enzyme ALDH1A3.

5. A pharmaceutical composition comprising at least one compound according to claim 1.

6. The compound according to claim 1 for use in the selective detection of enzyme ALDH1A3.

7. The compound according to claim 1 for use in resecting glioblastomas during surgery.

8. The compound according to claim 1 for use in diagnosing glioblastomas.

* * * * *